United States Patent
Liang

(10) Patent No.: US 6,222,058 B1
(45) Date of Patent: Apr. 24, 2001

(54) PROCESS FOR THE MANUFACTURE OF CYCLOPROPANECARBONITRILE

(75) Inventor: Shaowo Liang, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/050,269

(22) Filed: Mar. 30, 1998

(51) Int. Cl.$^7$ ............................................... C07C 253/02
(52) U.S. Cl. ................................................. 558/314
(58) Field of Search .................................. 558/314

(56) References Cited

U.S. PATENT DOCUMENTS

| | | |
|---|---|---|
| 3,853,942 | 12/1974 | Sury et al. . |
| 3,932,468 | 1/1976 | Kurkov . |
| 3,996,248 | 12/1976 | Wall et al. . |
| 4,205,009 | 5/1980 | Onore et al. . |
| 4,275,238 | 6/1981 | Petree et al. . |
| 4,897,498 | 1/1990 | Monnier et al. . |
| 4,950,773 | 8/1990 | Monnier et al. . |
| 5,082,956 | 1/1992 | Monnier et al. . |
| 5,254,701 | 10/1993 | Falling et al. . |
| 5,502,234 | 3/1996 | Liang . |

FOREIGN PATENT DOCUMENTS 1570319    6/1980   (GB) .

OTHER PUBLICATIONS

Ben H. Nicolet et al, J. Am. Chem. Soc., 1927, vol. 49, 2066–2071.
John B. Cloke, J. Am. Chem. Soc., 1929, vol. 51, 1174–1187.
Maurice J. Schlatter, J. Am. Chem. Soc., 1941, vol. 63, 1733–1737.
M. Mitani et al, J. Chem. Soc., Chem. Commun., 1983, 1446–1447.
H. Kanai et al, Bull. Chem. Soc. Japan, (1983), vol. 56, 1025–1029.
K. Mai et al, Tetrahedron Lett., 1986, vol. 27, 2203–2206.
T. Van Es, J. Chem. Soc., 1965, 1564.
G. A. Olah et al, Synthesis, 1979, 112–113.
T. Ando et al, J. Hazardous Materials, (1991), vol. 28, 251–280.
Wilson, J. Amer. Chem. Soc., 1947, vol. 69, 3002–3004.
J. B. Chattopadhyaya et al, Tetrahedron, 1974, vol. 30, 2899–2900.
J. P. De Kerrsmaeker et al, Ind. Chim. Belge, 1967, vol. 32, 1087.
Roger Adams et al, J. Amer. Chem. Soc., 1952, vol. 74, 694–699.
W. Wenner, Org. Synth. 1952, vol. 32, 92–94.

*Primary Examiner*—Joseph K. McKane
*Assistant Examiner*—Joseph Murray
(74) *Attorney, Agent, or Firm*—Michael J. Blake; Harry J. Gwinnell

(57) ABSTRACT

Disclosed is a process for the production of cyclopropanecarbonitrile (CPCN) by feeding concurrently cyclopropanecarboxaldehyde (CPCA) and hydroxylamine aqueous solution to a reaction zone which contains formic acid. The process avoids the formation and accumulation of large amounts CPCA oxime intermediates which exhibit a very high energy release upon thermal decomposition. Additional embodiments of the invention comprise the steps of (1) synthesizing CPCN by feeding concurrently CPCA and hydroxylamine aqueous solution to a reaction zone containing formic acid to form a reaction product mixture comprising CPCN and (2) isolating and recovering the CPCN by contacting the reaction product mixture with a base to obtain a mixture comprising an organic phase containing CPCN and an aqueous phase. The removal of an azeotrope vapor comprising CPCN, water and a minor amount of formic acid from the reaction product mixture reduces the amount of formic acid consumed in the process as well as the amount of formate salts generated by the process.

11 Claims, No Drawings

PROCESS FOR THE MANUFACTURE OF CYCLOPROPANECARBONITRILE

This invention pertains to a process for the production of cyclopropanecarbonitrile (CPCN). More specifically, this invention pertains to the production of CPCN by feeding concurrently cyclopropanecarboxaldehyde (CPCA) and hydroxylamine aqueous solution to a reaction zone which contains formic acid. The process avoids the formation and accumulation of large amounts CPCA oxime intermediates which exhibit a very high energy release upon thermal decomposition. Additional embodiments of the invention comprise the steps of (1) synthesizing CPCN by feeding concurrently CPCA and hydroxylamine aqueous solution to a reaction zone containing formic acid to form a reaction product mixture comprising CPCN and (2) isolating and recovery the CPCN.

CPCN has proven to be a valuable as well as versatile compound. For example, it is an important synthetic building block for introducing the cyclopropane ring into agricultural chemicals such as N-cycloalkyl anilines, whose performance characteristics are substantially improved by the presence of the cyclopropyl group.

Prior art methods for preparing CPCN have involved reacting, in general, a halobutyronitrile with a base such as alkali metal hydroxide (*J. Am. Chem. Soc.*, 1927, 49, 2068 and *J. Am. Chem. Soc.*, 1929, 51, 1174) or sodium amide (*J. Am. Chem. Soc.*, 1941, 63, 1734). However, certain problems have been encountered with these prior art procedures. For example, high temperatures normally are required for these reactions. Furthermore, substandard yields of product frequently have been obtained due to troublesome side reactions and difficult and prolonged distillation procedures.

U.S. Pat. No. 3,853,942 describes a process for the preparation of CPCN by reacting halobutyronitrile with an alkali metal alkoxide in an inert solvent at elevated temperatures and removing the alcohol formed. However, the alkali metal alkoxide is a relatively expensive reactant, which also is difficult to handle. U.S. Pat. No. 4,205,009 and GB 1,570,319 describe a similar process using alkali metal hydroxide instead of alkoxide in the presence of an anionic surfactant and an inert organic solvent. However, for better control of this phase-transfer reaction, environmentally unfriendly solvents such as benzene or dichloromethane are required. Furthermore, 4-halobutyronitrile (4-chloro- and 4-bromo-butyroniutile in particular) is used as the starting materials. Methods for preparing such nitrites are described in the *J. Am. Chem. Soc.* articles and U.S. Pat. No. 3,853,942 noted hereinabove. These nitriles typically are prepared by the anhydrous, free radical reaction of allyl chloride and hydrogen halide in the presence of benzoyl peroxide followed by the reaction of the resulting trimenthylenechlorohalide, in 500% excess, with sodium cyanide in ethanol-water medium. This method of preparing nitrites suffers from a number of disadvantages such as the handling of a corrosive hydrogen halide and highly toxic metal cyanide and difficult product isolation due to the formation of regeoisomers.

Additional procedures for the synthesis of CPCN on a laboratory scale involve a carbene insertion or Simmons-Smith reaction with acrylonitrile (see, for example, M. Mitain et al., *J. Chem. Soc., Chem Commun.*, 1983, 1446; H. Kanai et al. *Bull. Chem. Soc. Jpn.* 1983 56, 1025) or the dehydration of cyclopropanecarboxamide with the liquid "diphosgene", trichloromethyl chloroformate as dehydrating agent (K. Mai and G. P Atil, *Tetrahedron Lett.*, 1986, 27, 2203). While convenient for laboratory use, these procedures present serious safety concerns and/or require the use of expensive reagents when utilized on a commercial scale.

Prior art methods for preparing carbonitriles from aldehydes have involved, in general, (a) dehydration of aldoximes using diclohexylcarbodiimide, N,N'-carbonyldiimidazole, N,N-imethyldichloromethaniminmium chloride, phosphonitrile dichloride, phenylchlorosulfite or selenium dioxide; (b) 1,2-elimination of reactions of O-substituted aldoximes; (c) 1,2-elimination reactions of aldehyde trimethylhydrazonium iodides and aldehyde N-tosylimines using base; (d) conversion of aldehydes to nitrites using ammonialsodium methoxide in methanol containing iodine or using an amine imide as an oxidizing agent. Again, while convenient for laboratory use, these methods are not suitable for large-scale commercial use due to safety concerns and/or use of expensive reagents.

Aldehydes having the formula of R-CHO have been converted to nitriles having the formula to R-CN wherein R is aryl or acyclic alkyl, using hydroxylamine chloride with large quantity of formic acid as solvent in the presence or absence of sodium formate. These methods generally give reasonable yields and less side reactions when R is an aromatic moiety or a long aliphatic chain (Cn where n=/>4). For example, T. ven Es (*J. Chem. Soc.* 1965, 1564) describes a procedure of using 1.15 equivalents of hydroxylamine and excess sodium formate (2 equivalents) with large amounts of formic acid (33 equivalents) to give good yields of aromatic nitriles. However, the procedure gives poor yields (30%) of n-propanecarbonitrile. Preparation of CPCN is not mentioned. G. A. Olah and T. Keumi (*Synthesis* 1979, 112) describe a similar procedure (except no sodium formate is used) for the synthesis of aromatic nitriles and selected alkyl nitriles. In order to dissolve the hydroxylamine salt completely and to minimize side reactions, large amounts, e.g., 22 equivalents, of formic acid are required. It is very difficult, if not impossible, to isolate lower alkyl nitrites, e.g., nitrites containing a total of 2 to 4 carbon atoms, from formic acid either by extraction or distillation (formation of an azeotrope). Neutralization with a base (5% aqueous sodium hydroxide solution), as described in the procedure, will generate more than 20 equivalents of salts as wastes. Very intensive extractions are required for the product recovery of aliphatic nitrites. It is apparent that the commercial-scale use of the procedure described by Olah et al. would present serious problems.

Finally, U.S. Pat. No. 5,502,234 describes a process for the production of CPCN from CPCA in high selectivity and yield and for the recovery of the nitrile product. The process involves three steps comprising: (1) reacting CPCA with hydroxylamine base in the presence of water to obtain CPCA oxime; (2) contacting the CPCA oxime of step (1) with formic acid to obtain CPCN; and (3) contacting the mixture comprising CPCN formed in step (2) with a base to obtain a mixture comprising an organic phase containing CPCN and an aqueous phase. Although this process is useful for the preparation of CPCN, it presents safety problems due to the formation and accumulation of a large quantity of CPCA oxime intermediates. The CPCA oxime intermediates comprise the E and Z oxime isomers and, possibly, formate esters thereof It has been found that the CPCA oxime intermediates formed from in the process have a very high energy release upon thermal decomposition (1684 J/g with an onset temperature of 91° C. for E/Z isomers of 1:1 ratio). In the presence of formic acid, the onset temperatures are even lower (31–42° depending on the concentrations). The release of such large amounts of energy upon decomposition at relatively low initiation temperatures presents serious safety problems. For example, in commercial-scale operations, the loss of means of cooling and/or agitation could result in an explosive release of energy. Most organic oximes decompose exothermically with the release of large amounts of energy. For example, propionaldehyde oxime has a thermal decomposition energy of 2058 J/g with an onset temperature of 202° C. It has been reported (T. Ando at al., *J. Hazardous Materials*, 1991, 28, 251–280) that DSC testing has shown that 16 out of 18 organic oximes have an average energy release upon thermal decomposition of about 2000 J/g with an average onset temperature of 220° C. The release of large amounts of energy from thermal decomposition presents serious safety concerns for the production of CPCN on a commercial scale.

I have discovered that CPCN can be conveniently, safely and economically produced on a commercial scale by means of process in which CPCA and hydroxylamine are reacted in the presence of formic acid to form CPCA oxime intermediates which are dehydrated quickly by the formic acid to form CPCN. Accordingly, one embodiment of the present invention is a process for the preparation of CPCN which comprises feeding concurrently CPCA and aqueous hydroxylamine to a reaction zone containing formic acid to obtain a reaction product mixture comprising CPCN, water and formic acid. Second and third embodiments of the invention comprise the above-described CPCN synthesis step in combination with process steps for the recovery of the CPCN thus produced. In the process of the present invention, the CPCA oximes form quickly from CPCA and hydroxylamine (E and Z oximes form in about 1:1 ratio) and the oxime intermediates dehydrate rapidly in the presence of formic acid to form CPCN. Thus, the oxime accumulation can be controlled and maintained as a very low level throughout the entire process. For example, the oxime concentration in the reaction medium or mixture may be controlled at a level of less than 5 weight percent of the total weight of the reaction mixture at any given time during the reaction without compromising throughput and yields. As a result, no hazardous, run-away, thermal decomposition can take place even if a loss of cooling and/or loss of agitation occurs during the process.

The starting material for the present process, CPCA, may be obtained by the thermal rearrangement of 2,3-dihydrofuran. For example, U.S. Pat. No. 4,275,238 describes passing 2,3-dihydrofuran through a column at 480° C. to obtain CPCA having a purity of 90% purity and containing 6.2–6.7% crotonaldehyde. A similar procedure is described by Wilson (*J. Amer. Chem. Soc.* 1947, 69, 3002). 2,3-Dihydrofuran may be obtained according to the process described in U.S. Pat. No. 5,254,701 by the isomerization of 2,5-dihydrofuran which in turn can be produced by the isomerization of 3,4-epoxy-1-butene as described in U.S. Pat. Nos. 3,932,468, 3,996,248 and 5,082,956. U.S. Pat. Nos. 4,897,498 and 4,950,773 describe the preparation of 3,4-epoxy-1-butene by selective monoepoxidation of butadiene.

The bydroxylamine free base employed in the process of this invention may be a provided as an aqueous solution containing about 10 to 80 weight percent, preferably 30 to 50 weight percent, hydroxylamine free base aqueous solution. The hydroxylamine free base may be generated in situ by treating an acid salt of hydroxylamine with a base such as an alkali metal hydroxide, preferably sodium hydroxide. Hydroxylamine salts include its salts formed from an inorganic acid such as sulfuric acid, hydrochloric acid, nitric acid, and phosphoric acid or formed from an organic acid such as formic acid, acetic acid, propionic acid, and sulfonic acids. Examples of these hydroxylamine salts include hydroxylamine sulfate, hydroxylamine hydrochloride, hydroxylamine phosphate, hydroxylamine nitrate and hydroxylamine formate etc. The advantage of using hydroxylamine free base (either as an aqueous solution or generated in situ from its salt) is to avoid the generation of strong acids during the oxime formation when hydroxylamine acid salts are used. Such acids typically cause side reactions such as, for example, ring cleavage by HCl to give 4-chlorobutyronitrile, Beckmann rearrangement to give cyclopropanecarboxamide and strong acid-catalyzed hydrolysis of the product nitrile to the corresponding carboxamide and/or carboxylic acid. It is known that oximes of lower alkyl aldehydes, e.g. $C_2$–$C_4$ aldehydes, such as acetaldehyde (J. B. Chattopadhyaya, and A. V. Rama Rao, *Tetrahedron* 1974, 30, 2899), propionaldehyde and butyraldehyde (I. P. De Keersmaeker, and F. Fontyn, *Ind. Chim. Belge*, 1967, 32, 1087) mainly form the corresponding amides via Beckmann rearrangement under acid-catalyzed conditions. It is well known that nitriles, especially lower alkyl nitrites readily undergo hydrolysis in the presence of strong acids such as sulfuric acid and hydrochloric acid (*J. Amer. Chem. Soc.* 1952, 74, 694; W. Wenner, *Org. Synth.* 1952, 32, 92).

Formic acid functions in the process of the invention as both a dehydrating agent and a solvent. It is believed that the oxime and formic acid form an intermediate ester which facilitates nitrile formation by an intra-molecular (six member-ring transition state) elimination of formic acid. The purity or concentration of the formic acid used typically is at least 80 weight percent and preferably at least 90 weight percent. In commercial operation of the process, a range of about 1 to 2 equivalents of formic acid will give short reaction time, good selectivity and easy product isolation without generating large amounts of by-product formate salts generated in the recovery of the CPCN.

The concurrent addition CPCA and hydroxylamine to the reaction zone containing formic acid may be intermittent or, preferably, substantially continuous. The rate of addition of CPCA and hydroxylamine should give a CPCA:hydroxylamine mole feed ratio of about 1:0.5 to 1:5, preferably about 1:0.8 to 1:1.2, for any given period of time. The use of feed rates outside of these ratios can result in a substantial loss in yield due to decomposition of the reactant which is in excess in the formic acid-containing reaction zone. With the proper engineering design, the CPCA and aqueous hydroxylamine may be added concurrently in a manner wherein the CPCA and hydroxylamine are combined at a point immediately preceding the reaction zone or immediately prior to contacting the formic acid. The process is carried out while maintaining the reaction mixture of the reaction zone at a temperature in the range of about 20 to 160° C., preferably about 80 to 120° C. The reaction zone may be maintained at pressures moderately below or above atmospheric pressure, e.g., from about 0.3 to 4.5 bars absolute, although excellent production rates are achieved at ambient pressure. The reaction zone preferably comprises a plurality of reactors arranged in series wherein at least 95 weight percent, preferably 99 weight percent of oxime intermediates are converted to CPCN.

The total amount of CPCA and aqueous hydroxylamine reactants which may be fed concurrently to an initial quantity of formic acid, i.e., without removing reaction product mixture periodically or continuously from the reaction zone, typically will give a final reaction mixture containing up to a maximum of 80 weight percent CPCN, preferably about 10 to 50 weight percent CPCN. Operation of the process may be modified by removing, periodically or continuously, CPCN-containing reaction mixture from the reaction zone and replacing the reaction mixture removed with fresh formic acid. This mode of operation wherein CPCA, aqueous hydroxylamine and formic acid are fed intermittently or continuously to a reaction zone and CPCN-containing reaction mixture is removed intermittently or continuously from the reaction zone permits continuous operation of the process over prolonged periods of time. Normally, the process is operated in a manner whereby the amount of water present in the reaction mixture does not exceed about 50 weight percent of the mixture.

The second embodiment of the present invention comprises the above-described CPCN-synthesis step in combination with a product recovery step wherein crude reaction product mixture (containing CPCN, formic acid and water) resulting from the synthesis step is contacted with a base to obtain a mixture comprising an organic phase containing CPCN and an aqueous phase. Most, e.g., up to 98 weight percent, of the CPCN formed is obtained in the organic phase. This product isolation step normally is carried out at a temperature of less than about 75° C., preferably in the range of about 30 to 55° C. Examples of the bases which may be used in the third step include the alkali metal hydroxides and carbonates and the alkaline earth metal hydroxides and carbonates. The hydroxides and carbonates of sodium, potassium, cesium, magnesium and calcium are specific examples of useful bases. The alkali metal hydroxides and, especially, sodium hydroxide, represent the most preferred bases.

The amount of base utilized in the product isolation step typically gives an equivalent of base per mole of formic acid used in the first step of about 0.5:1 to about 2:1, preferably about 0.8:1 to 1.2:1. The term "equivalent" is used herein to specify the stoichiometric amount of base required to neutralize 1 mole of formic acid. For example, a mole of alkali metal hydroxide constitutes 1 equivalent of base whereas 1 mole of alkali metal carbonates and alkaline earth metal hydroxides and carbonates constitutes 2 equivalents of base. Although the base can be used in step (3) in the form of a finely divided solid, it more conveniently is used as an aqueous solution, e.g., in base concentrations of up to 90 weight percent, depending upon the particular base used. The concentration of the preferred alkali metal hydroxides in the aqueous alkali metal hydroxide solutions preferably is about 40 to 60 weight percent. A 50 weight percent aqueous sodium hydroxide solution is the most preferred alkali metal hydroxide solution.

The organic layer of the two-phase mixture formed in the product isolation step can be isolated by known recovery procedures. The organic phase (upper layer) comprises about 80 to 95 weight percent CPCN. It is possible to use the crude CPCN contained in the organic phase without further purification. Normally, however, the CPCN-containing phase is purified, e.g., by fractional distillation to obtain CPCN having a purity of greater than 99%, prior to the conversion of the CPCN to other chemical compounds. The aqueous phase of the two-phase mixture can be extracted with a suitable water-immiscible solvent to recover addition CPCN. Examples of suitable water-immiscible extractants include tertiary butyl methyl ether, diethyl ether, diisopropyl ether, alkyl acetates such as propyl and isopropyl acetate, toluene, benzene, diethoxymethane and alkyl nitriles such as acetonitrile and butyronitrile. Alternatively, CPCN present in the aqueous phase may be recovered by stripping off about 1 to 5 weight percent of the total aqueous phase as an azeotrope.

A third embodiment of the present invention comprises the above-described CPCN synthesis step in combination with a product isolation step wherein crude reaction product mixture (containing CPCN, water and formic acid) resulting from the synthesis step is removed from the reaction zone as a vapor, the vapor is condensed and the condensate is treated with base, as described previously relative to the second embodiment, to recover the CPCN product. For example, The vapor may be produced by heating the crude reaction mixture within the reaction zone vessel which contains from about 5 to 95 weight percent CPCN. The CPCN-containing vapor may be generated in and removed from one or more reaction vessels of the reaction zone. Alternatively, the crude product may be removed as a liquid from the reaction zone and fed to a separate distillation vessel wherein a minor portion of the crude product mixture is vaporized and the remainder of the crude product mixture is returned to the reaction zone.

The third embodiment of the present invention therefore comprises the steps of (1) feeding concurrently cyclopropanecarboxaldehyde (CPCA) and aqueous hydroxylamine to a reaction zone containing formic acid to obtain a reaction product mixture comprising CPCN, water and formic acid; (2) removing a vapor of the reaction product mixture comprising CPCN, water and and a minor amount of formic acid from the reaction zone; (3) condensing the vapor of step (2) to obtain a liquid comprising CPCN, water and and a minor amount of formic acid; and (4) contacting the liquid of step (3) with a base to obtain a mixture comprising an organic phase containing CPCN and an aqueous phase wherein the equivalents of base per mole of formic acid used in step (4) is in the range of 0.5:1 to 2:1. The vapor comprises a ternary constant boiling mixture (azeotrope) having a boiling point in the range of about 97 to 102° C. at ambient pressure and comprising CPCN, water and a minor amount of formic acid. The composition of the azeotrope appears to vary, depending upon the pressure at which the vapor is generated. Generally, the composition is comprised of about 30 to 60 weight percent CPCN, 40 to 70 weight percent water and 1 to 15 weight percent formic acid. This third embodiment is advantageous since the amount of formic acid which is treated with base and neutralized is substantially less than the amount of formic acid which is treated with base in accordance with the second embodiment of the present invention. When compared with the process of the second embodiment, this highly advantageous feature of the third embodiment results in a substantial reduction in both formic acid usage and the amount of formate salts generated in the recovery process. For example, for every kg of CPCN produced by the process of the third embodiment, less than 0.1 kg of formic acid is consumed.

The processes of the present invention provide an economical and safe means for the production of cyclopropanecarbonitrile. The processes avoid the use of expensive reagents that are difficult to handle and avoid potential safety problems posed by potential thermal decomposition of oxime intermediates. The processes are carried out under mild conditions using relatively simple product isolation procedures and generate limited amounts of waste. Most importantly the processes of this invention can be performed safely on a commercial production scale.

The processes provided by the present invention are further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic spectrometry and gas chromatography-mass spectrometry by comparison to authentic samples purchased from Aldrich Chemical Company.

EXAMPLE 1

To a 3-liter, 4-necked flask equipped with an overhead stirrer, a thermometer and a condenser was placed 90% formic acid (511.1 g, 10.0 mole). The formic acid was heated to 90° C. To the preheated formic acid were added CPCA (94% assay, containing 6% crotonaldehyde, 350g, 4.7 mole) and 50% hydroxylamine aqueous solution (346.5 g, 5.25 mole) concurrently by two pumps over a period of 5 hours while maintaining the reaction temperature at 90–95° C. After the completion of the addition, the reaction mixture was heated to refluxing (102–105° C.) for 2 hours. After cooling to room temperature, the mixture was neutralized with 50% aqueous sodium hydroxide solution (760 g, 9.5 mole) to pH 9–10 while controlling the temperature at less than 50° C. Two phases rapidly formed and separated. The organic phase (305.69 g, 91.72 weight percent CPCN) was further purified by distillation to give pure CPCN. An additional 18.93 g of pure CPCN was recovered from the aqueous phase and the distillation residue by azeotropic distillation followed by further purification. A total of 285.30 g CPCN having a purity greater than 99% was obtained from the reaction which represented a 90.6% yield based on the amount of CPCA used.

EXAMPLE 2–10

To a 22-liter, 4-necked, jacketed flask equipped with an overhead stirrer, a thermometer and a condenser was placed 90% formic acid (5111 g, 100 mole). The formic acid was heated to 90° C. To the preheated formic acid were added CPCA (94% assay, containing 6% crotonaldehyde, 3500 g, 47.0 mole) and 50% hydroxylamine aqueous solution (3465 g, 52.5 mole) concurrently by two pumps over a period of 2 hours while maintaining the reaction temperature at 90–95° C. with water cooling through the jacket. After the completion of addition, the reaction mixture was heated at 90–95° C. for 4 hours. After cooling to room temperature, the mixture is neutralized with 500% aqueous sodium hydroxide solution (7600 g, 95.0 mole) to pH 9–10 while controlling the temperature at less than 50° C. Two phases formed rapidly and were separated.

The procedure described above was repeated eight times. The amount of crude CPCN (g) obtained as the organic phases, and the purity thereof (weight percent CPCN) and the % yield before distillation in each of the nine experiments are shown in Table I.

TABLE I

| Example No. | Crude CPCN | | |
|---|---|---|---|
| | Weight | Purity | Yield |
| 2 | 2995 | 96.22 | 92.50 |
| 3 | 3043 | 96.59 | 94.34 |
| 4 | 2869 | 97.79 | 90.05 |
| 5 | 2933 | 97.43 | 91.72 |
| 6 | 2990 | 97.20 | 93.29 |
| 7 | 2988 | 97.13 | 93.16 |
| 8 | 2913 | 97.37 | 91.04 |
| 9 | 2945 | 97.95 | 92.59 |
| 10 | 2892 | 97.64 | 90.64 |

The crude CPCN from Examples 2–10 was combined and distilled using a column containing 48 inches (1.22 meter) of Penn State packing to give 23,339 g CPCN having a purity of greater than 990%. The aqueous phases from Examples 2–10 were combined and subjected to azeotropic distillation followed by fractional distillation to give an additional 1077 g CPCN having a purity greater than 99%. The total yield of CPCN (having a purity greater than 99%) was 24416 g which is 87.1% of theory.

EXAMPLE 11

To a 3-liter 4-necked flask equipped with an over head stirrer, a thermometer and a condenser was placed 90% formic acid (613.3 g, 12.0 mole). The formic acid was heated to 100–105° C. To the preheated formic acid were added CPCA (420.6 g, 99% assay, 6.0 mole, 0.02 mole/minute) and 50% hydroxylamine aqueous solution (436.0 g, 6.6 mole, 0.022 mole/minute) concurrently by two pumps over a period of 5 hours while maintaining the reaction mixture at 100–105° C. After the addition was complete, the reaction mixture was heated to refluxing (100–105° C.) for 2 hours. Samples were taken every 30 minutes during the reaction for GC analysis to determine the weight percent concentration of product CPCN and CPCA oxime in the reaction mixture. The results are shown in Table II wherein Reaction Time is given in minute, Total weight of Reaction Mixture values are grams and the values given for CPCN Conc. And Oxime Conc. Are weight percentages of CPCN and CPCA oximes, respectively, in the reaction mixture. After cooling to room temperature, the mixture is worked up and purified as described in Example 1 to give 379 g (99.5% purity) CPCN in 94% yield.

TABLE II

| Reaction Time | Total Weight of Reaction Mixture | CPCN Conc. | Oxime Conc. |
|---|---|---|---|
| 0 | 613.3 | 0.00 | 0.00 |
| 30 | 698.96 | 4.06 | 2.15 |
| 60 | 784.62 | 7.39 | 3.63 |
| 90 | 870.28 | 12.30 | 1.98 |
| 120 | 955.94 | 15.19 | 2.07 |
| 150 | 1041.6 | 17.98 | 2.18 |
| 180 | 1127.26 | 19.62 | 2.25 |
| 210 | 1212.92 | 21.11 | 2.65 |
| 240 | 1298.58 | 22.87 | 2.40 |
| 270 | 1384.24 | 23.69 | 3.11 |
| 300 | 1469.9 | 24.93 | 3.07 |
| 330 | 1469.9 | 26.10 | 1.75 |
| 360 | 1469.9 | 26.92 | 0.65 |
| 390 | 1469.9 | 27.25 | 0.16 |
| 420 | 1469.9 | 27.35 | 0.00 |
| 450 | 1469.9 | 27.35 | 0.00 |

EXAMPLE 12

To a 300 mL, 4-necked flask equipped with an over head stirrer, a thermometer and a distillation head was placed 90% formic acid (51.1 g, 1 mole). The formic acid was heated to 102–105° C. To the preheated formic acid were added CPCA (>99% assay 35.0 g, 0.5 mole) and 50% hydroxylamine aqueous solution (34.7 g, 0.53 mole) concurrently by two pumps over a period of 1 hour while maintaining the reaction temperature at 102–105° C. After the addition was complete, the reaction mixture was heated to refluxing (102–105° C.) for 2 hours. GC analysis indicated that the reaction was complete. The reaction mixture contains mainly CPCN, formic acid and water. To this mixture were added CPCA (13.9 g per hour) and hydroxylamine 50% aqueous solution (13.1 g per hour) via two pumps. At the same time, a vapor effluent comprising CPCN product, water and a small amount of formic acid was taken off as an azeotrope from the distillation head at a rate of 31 g per hour. The azeotrope consisted of 53 weight percent water, 43 weight percent CPCN and 4 weight percent formic acid. The azeotrope is condensed fed continuously to a decanter in which the formic acid was neutralized continuously with 50% aqueous sodium hydroxide solution while maintaining the temperature of the mixture below 50° C. After 20 hours of operation, a total of 278 g CPCA and 262 g 50% hydroxylamine, along with 25 g of 90% formic acid in 55 g water (to replace the formic acid and water in the azeotrope removed during the operation of the process) had been pumped into the reaction flask. A total of 620 g of liquid were condensed from the azeotrope effluent removed from the reaction flask. Upon neutralization, this liquid yielded 266 g of organic phase containing 93% CPCN. An additional 12 g of CPCN (90% purity) was recovered from the aqueous phase by azeotropic distillation. Fraction distillation of the combined crude CPCN gave 244 g of 99.5% pure CPCN (91% yield). The materials remaining in the reactor were primarily CPCN, formic acid and water which can be used for further continuous production of CPCN or from which CPCN can be recovered according to the procedures described.

EXAMPLE 13

To a 2-liter, 4-necked flask equipped with an over head stirrer, a thermometer and a distillation head was placed 90% formic acid (511.1 g, 10 mole) and CPCN (270 g, 99% assay). The mixture was heated to 102–105° C. To this mixture were added concurrently CPCA (139 g per hour), bydroxylamine 50% aqueous solution (131 g per hour) and 28% formic acid (40 g per hour) via three pumps while maintaining the reaction mixture at reflux (102–105° C.). At the same time, a vapor effluent comprising CPCN product, water and a small amount of formic acid, was removed from the distillation head as an azeotrope at a rate of 310 g per hour. The azeotrope consists of 53 weight percent water, 43 weight percent CPCN and 4 weight percent formic acid. The azeotrope is condensed and fed continuously to a decanter wherein the formic acid was neutralized continuously with 50% zqueous sodium hydroxide solution while keeping the temperature of the mixture below 50° C. After 20 hours of operation, a total of 2780 g CPCA, 2620 g of 50% hydroxylamine and 800 g of 28% formic acid (prepared by mixing 90% formic acid with water) had been pumped into the reactor. A total 6200 g of azeotrope/distillate were removed from the reaction flask. Neutralization (430 g of 50% aqueous sodium hydroxide were used) of the 6200 g of distillate gave 2668 g of organic phase which contained 93% CPCN. The aqueous phase (3960 g) was stripped by heating at 102–106° C. until the vapor temperature reached 97° C. to recover an azeotrope/distillate (265 g) having a boiling point of approximately 93–95° C. The distillate separated into two phases and the organic phase (125 g) consisting of 90 weight percent CPCN was recovered by decantation. Fractional distillation of the combined crude CPCN gave 2450 g of CPCN (99.6% purity, 92% of theory). The materials remaining in the reactor comprise primarily CPCN, formic acid and water which can be use for further operation of the process or from which the CPCN may be recovered.

EXAMPLE 14

The procedure described in Example 1 is repeated except that the reaction flask also is equipped with an addition funnel. CPCN and aqueous hydroxylamine are pumped concurrently into the addition funnel which allowed mixing of the CPCA and hydroxylamine for about 1–3 seconds before entering the reaction flask containing formic acid. The yield and quality of the CPCN thus produced is substantially the same as that obtained in Example 1.

The invention has been described in detail with particular reference to preferred embodiments thereof, but it will be understood that variations and modifications can be effected within the spirit and scope of the invention.

I claim:

1. Process for the preparation of cyclopropanecarbonitrile (CPCN) which comprises feeding concurrently cyclopropanecarboxaldehyde (CPCA) and aqueous hydroxylamine to a reaction zone containing formic acid to obtain a reaction product mixture comprising CPCN, water and formic acid.

2. Process according to claim 1 wherein the rate of addition of CPCA and hydroxylamine gives a CPCA:hydroxylamine mole feed ratio of about 1:0.5 to 1:5 and the reaction mixture within the reaction zone is maintained at a temperature of about 20 to 160° C.

3. Process according to claim 1 wherein the rate of addition of CPCA and hydroxylamine gives a CPCA:hydroxylamine mole feed ratio of about 1:0.8 to 1:1.2 and the reaction mixture within the reaction zone is maintained at a temperature of about 80 to 120° C.

4. Process for the preparation and recovery of cyclopropanecarbonitrile (CPCN) which comprises the steps of (1) feeding concurrently cyclopropanecarboxaldehyde (CPCA) and aqueous hydroxylamine to a reaction zone containing formic acid to obtain a reaction product mixture comprising CPCN, water and formic acid and (2) contacting the reaction product mixture with a base to obtain a mixture comprising an organic phase containing CPCN and an aqueous phase wherein the equivalents of base per mole of formic acid used in step (2) is in the range of 0.5:1 to 2:1.

5. Process according to claim 4 wherein the rate of addition of CPCA and hydroxylamine in step (1) gives a CPCA:hydroxylamine mole feed ratio of about 1:0.5 to 1:5 and the reaction mixture within the reaction zone is maintained at a temperature of about 20 to 160° C.

6. Process according to claim 4 wherein the rate of addition of CPCA and hydroxylamine in step (1) gives a CPCA:hydroxylamine mole feed ratio of about 1:0.8 to 1:1.2 and the reaction mixture within the reaction zone is maintained at a temperature of about 80 to 120° C. and the base in step (2) is selected from the alkali metal hydroxides and carbonates and the alkaline earth metal hydroxides and carbonates.

7. Process according to claim 6 wherein step (2) is carried out at a temperature of less than 75° C. and the base is aqueous sodium hydroxide.

8. Process for the preparation and recovery of cyclopropanecarbonitrile (CPCN) which comprises the steps of (1) feeding concurrently cyclopropanecarboxaldehyde (CPCA) and aqueous hydroxylamine to a reaction zone containing formic acid to obtain a reaction product mixture comprising CPCN, water and formic acid; (2) removing a vapor of the reaction product mixture comprising CPCN, water and and a minor amount of formic acid from the reaction zone; (3) condensing the vapor of step (2) to obtain a liquid comprising CPCN, water and and a minor amount of formic acid; and (4) contacting the liquid of step (3) with a base to obtain a mixture comprising an organic phase containing CPCN and an aqueous phase wherein the equivalents of base per mole of formic acid used in step (4) is in the range of 0.5:1 to 2:1.

9. Process according to claim 8 wherein the rate of addition of CPCA and hydroxylamine in step (1) gives a CPCA:hydroxylamine mole feed ratio of about 1:0.5 to 1:5 and the reaction mixture within the reaction zone is maintained at a temperature of about 20 to 160° C.

10. Process according to claim 8 wherein the rate of addition of CPCA and hydroxylamine in step (1) gives a CPCA:hydroxylamine mole feed ratio of about 1:0.8 to 1:1.2 and the reaction mixture within the reaction zone is maintained at a temperature of about 80 to 120° C. and the base in step (4) is selected from the alkali metal hydroxides and carbonates and the alkaline earth metal hydroxides and carbonates.

11. Process according to claim 10 wherein step (4) is carried out at a temperature of less than 75° C. and the base is aqueous sodium hydroxide.

* * * * *